United States Patent [19]
Li et al.

[11] Patent Number: 6,008,321
[45] Date of Patent: Dec. 28, 1999

[54] UNIVERSAL LINKER FOR COMBINATORIAL SYNTHESIS

[75] Inventors: Ge Li, Lawrenceville; Sian Louise Griffiths, Plainsboro; Edward McDonald, Lawrenceville; Libo Xu, Plainsboro, all of N.J.

[73] Assignee: Pharmacopeia, Inc., Princeton, N.J.

[21] Appl. No.: 09/039,837

[22] Filed: Mar. 16, 1998

[51] Int. Cl.$^6$ ............... G01N 33/543; G01N 33/545; C07C 59/48; C07C 59/56; C07C 233/00

[52] U.S. Cl. ............... 530/334; 436/531; 436/518; 436/523; 530/335; 562/426; 562/431; 562/466; 562/471; 562/472; 564/123; 564/161; 564/162; 564/163; 568/583; 568/626; 568/630; 568/667

[58] Field of Search ............... 436/518, 523–531; 530/334, 335; 562/426, 431, 466, 471–472; 564/123, 161–163; 568/583, 626, 630, 667

[56] References Cited

FOREIGN PATENT DOCUMENTS 0689845 of 1996 European Pat. Off. .
WO95/34577 of 1995 WIPO .

OTHER PUBLICATIONS

Zaho et al. "Soluble polymer synthesis: an improved traceless linker methodology . . . " *Tetrahedron Lett.* 38, 97–980 (1997).

Florsheimer et al. "Solid–phase synthesis of peptides with the highly . . . " *Peptides* 131–133 (1990).

Sharma et al. "Reductive Amination with Tritylamine as an Ammonia Equivalent: . . . " *J. Org. Chem.* 58, 4993–4996 (1993).

Flechsler et al. "Anchor–linked Intermediates in Peptide Amide Synthesis are Caused . . . " *J. Pept. Sci.* 3, 191–200 (1995).

Seitz et al. "Chemoenzymatic Solution—and Solid–Phase Synthesis of . . . " *J. Am. Chem. Soc.* 119, 8766–8776 (1997).

Ngu et al. "Preparation of Acid—labile Resins with Halide Linkers and . . . " *Tetrahedron Lett.* 38, 973–976.

Raju et al. "Use of Halomethyl Resins to Immobilize Amines: An . . . " *Tetrahedron Lett.* 38, 4965–4968 (1977).

Backes et al. "Solid support linker strategies" *Current Opinion in Chemical Biology* 1, 86–93 (1997).

Chen et al. *J. Amer. Chem. Soc.*, 1994, vol. 116, pp. 2661–2662, 1994.

Riniker, B. et al., "A General Strategy for the Synthesis of Large Peptides: The Combined Solid–Phase and Solution Approach," *Tetrahedron*, 49:9307–9320 (1993).

*Primary Examiner*—Keith D. MacMillan
*Assistant Examiner*—Maurie E. Garcia
*Attorney, Agent, or Firm*—Heslin & Rothenberg, P.C.

[57] ABSTRACT

A substrate for solid phase synthesis of the formula:

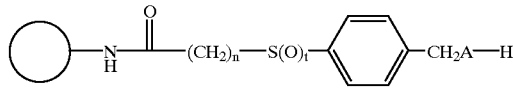

is disclosed. Also disclosed are processes for preparing the substrate and intermediates useful therein. Among the novel intermediates are compounds of the formula:

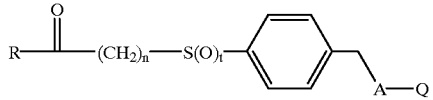

wherein t is 0 or 1; n is 3–20; R is OH, an activated ester or the residue of a solid support having a plurality of amino functionalities; A is —O— or —NH— and Q is hydrogen or a protecting group for an amine or alcohol.

7 Claims, No Drawings

UNIVERSAL LINKER FOR COMBINATORIAL SYNTHESIS

TECHNICAL FIELD

This invention relates generally to the synthesis of chemical compounds, and more particularly, to the solid phase synthesis of combinatorial libraries of chemical compounds.

BACKGROUND OF THE INVENTION

Combinatorial organic synthesis is becoming an important tool in drug discovery. Methods for the synthesis of large numbers of diverse compounds have been described [Ellman, et. al. *Chem. Rev.* 96: 555–600 (1996)], as have methods for tagging systems [Ohlmeyer et al., *Proc. Natl. Acad. Sci.* USA, 90, 10922–10926, (1993)]. The growing importance of combinatorial synthesis has created a need for new resins and linkers having chemical and physical properties to accommodate a wide range of conditions, since success depends on the ability to synthesize diverse sets of molecules on solid supports and to then cleave those molecules from the supports clearly and in good yield.

Linkers are molecules that can be attached to a solid support and to which the desired members of a library of chemical compounds may in turn be attached. When the construction of the library is complete, the linker allows clean separation of the target compounds from the solid support without harm to the compounds and preferably without damage to the support. Several linkers have been described in the literature. Their value is constrained by the need to have sufficient stability to allow the steps of combinatorial synthesis under conditions that will not cleave the linker, while still having a fairly high lability under at least one set of conditions that is not employed in the synthesis. For example, if an acid labile linker is employed, then the combinatorial synthesis must be restricted to reactions that do not require the presence of an acid of sufficient strength to endanger the integrity of the linker. This sort of balancing act often imposes serious constraints on the reactions that can be employed in preparing the library.

The 4-[4-(hydroxymethyl)-3-methoxyphenoxy]butyryl residue is a known linker, which is attached to a solid support having amino functionalities by forming an amide with the carboxyl of the butyric acid chain. N-Protected amino acids are attached to the hydroxyl of the 4-hydroxymethyl group via their carboxyl to form 2,4-dialkoxybenzyl esters, which can be readily cleaved in acid media when the synthesis is complete [see for example Riniker et al. *Tetrahedron* 49 9307–9312 (1993)]. The drawback to such 2,4-dialkoxybenzyl esters is that they can also be cleaved by many of the reagents that one might want to use in combinatorial synthesis.

A somewhat more stable ester is formed from 4-[4-(hydroxymethyl)phenoxy]butyric acid. It has been described in European published application EP 445915. In this case, the ester was cleaved with a 90:5:5 mixture of trifluoroacetic acid, dimethyl sulfide and thioanisole.

When the desired product is a peptide amide, the 4-[4-(formyl)-3,5-dimethoxyphenoxy]butyryl residue has been employed. It is attached to a solid phase substrate via the carboxyl of the butyric acid chain, and the 4-aldehyde is reductively aminated. N-Protected amino acids are then reacted with the alkylamine via their carboxyl to form 2,4,6-trialkoxybenzylamides. These may be cleaved by 1:1 trifluoroacetic acid in dichloromethane. [See PCT application WO97/23508.]

It would be useful to have a linker-resin combination that would withstand a wider range of reaction conditions in combinatorial synthesis, but that could be readily and cleanly cleaved following completion of the solid phase synthesis.

SUMMARY OF THE INVENTION

The present invention relates to a linker-resin combination that demonstrates the ability to withstand many of the common reaction conditions and yet is cleavable under relatively mild conditions. In the following disclosure, the variables are defined when introduced and retain that definition throughout.

In one aspect, the invention relates to a substrate for solid phase synthesis comprising a solid phase-linker combination of the formula:

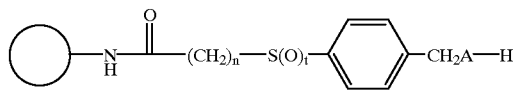

wherein

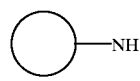

represents the residue of a solid support having a plurality of amino functionalities and the remainder constitutes the linker.;

A is —O— or —NH—;

n is 3–20, preferably 3–5; and t is 0 or 1. Preferred solid phases are aminomethylated poly(styrene-co-divinylbenzene) and divinylbenzene-cross-linked, polyethyleneglycol-grafted polystyrene functionalized with amino groups.

In another aspect, the invention relates to chemical intermediates of the formula VI

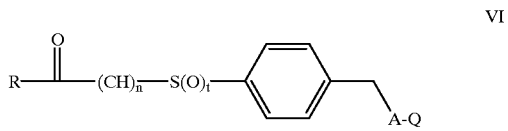

wherein Q is hydrogen or a protecting group for an amine or alcohol; and R is chosen from OH, the residue of a solid support having a plurality of amino functionalities, and a residue of an activated ester. Preferred activated ester residues are those of pentafluorophenol, N-hydroxysuccinimide and hydroxybenzotriazole:

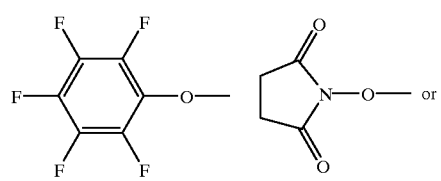

-continued

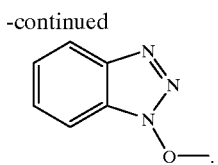

When A is NH, Q is preferably t-butoxycarbonyl or benzyloxycarbonyl; when A is —O—, Q is preferably aryl- or alkylcarbonyl (e.g. benzoyl or acetyl), benzyl, t-butyl, tetrahydropyranyl or trialkylsilyl.

In another aspect, the invention relates to processes for preparing the foregoing substrate for solid phase synthesis. One process comprises:

(a) combining in a suitable solvent a condensing agent, a solid support having a plurality of amino functionalities, and a compound of formula IV (i.e. VI in which R=OH)

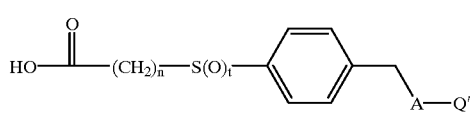

IV wherein Q' is a protecting group for an amine or alcohol to provide a protected precursor of a substrate for solid phase synthesis; and (b) treating the protected precursor with a reagent capable of cleaving the protecting group Q to provide a substrate for solid phase synthesis. In an alternative process, in step (a) a subset of VI in which R is a group displaceable by an amine ($R^4$) and no condensing agent is needed. Typically $R^4$ will be an activated ester and preferred activated esters are those shown above.

In another aspect, the invention relates to a process for solid phase synthesis comprising:

(a) reacting a substrate for solid phase synthesis of the formula:

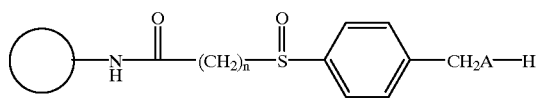

with a reagent capable of reacting with an amine or alcohol to provide a support-linked synthon;

(b) carrying out a plurality of chemical transformations on the support-linked synthon to provide a support-linked product;

(c) treating the support-linked product with a trivalent phosphorus reagent, whereby the sulfoxide is reduced to a thioether; and (d) treating the support-linked product with acid to cleave the product from the support and linker. Preferred trivalent phosphorus reagents are tributyl phosphine and triphenylphosphine. Trifluoroacetic acid is a preferred acid for cleavage.

DETAILED DESCRIPTION OF THE INVENTION

Abbreviations and Definitions

The following abbreviations and terms have the indicated meanings throughout:

Ac=acetyl
BNB=4-bromomethyl-3-nitrobenzoic acid
Boc=t-butyloxy carbonyl
Bu=butyl
c-=cyclo
DBU=diazabicyclo[5.4.0]undec-7-ene
DCM=dichloromethane=methylene chloride=$CH_2Cl_2$
DEAD=diethyl azodicarboxylate
DIC=diisopropylcarbodiimide
DIEA=N,N-diisopropylethyl amine
DMAP=4-N,N-dimethylaminopyridine
DMF=N,N-dimethylformamide
DMSO=dimethyl sulfoxide
DVB=1,4-divinylbenzene
EEDQ=2-ethoxy-1-ethoxycarbonyl-1,2-dihydroquinoline
Fmoc=9-fluorenylmethoxycarbonyl
GC=gas chromatography
HATU=O-(7-Azabenzotriazol-1-yl)-1,1,3,3-tetramethyluronium hexafluorophosphate
HOAc=acetic acid
HOBt=hydroxybenzotriazole
MCPBA=meta-chloroperbenzoic acid
Me=methyl
mesyl=methanesulfonyl
NMO=N-methylmorpholine oxide
PEG=polyethylene glycol
Ph=phenyl
PhOH=phenol
PfP=pentafluorophenol
PyBroP=bromo-tris-pyrrolidino-phosphonium hexafluorophosphate
rt=room temperature
sat'd=saturated
s-=secondary
t-=tertiary
TBDMS=t-butyldimethylsilyl
TFA=trifluoroacetic acid
THF=tetrahydrofuran
TMOF=trimethyl orthoformate
TMS=trimethylsilyl
tosyl=p-toluenesulfonyl
Trt=triphenylmethyl "Alkyl" is intended to include linear, or branched hydrocarbon structures and combinations thereof of 1 to 20 carbons. "Lower alkyl" means alkyl groups of from 1 to 6 carbon atoms. Examples of lower alkyl groups include methyl, ethyl, propyl, isopropyl, butyl, s-and t-butyl, pentyl, hexyl, and the like.

"Cycloalkyl" refers to saturated hydrocarbons of from 3 to 12 carbon atoms having one or more rings. Examples of "cycloalkyl" groups include c-propyl, c-butyl, c-pentyl, c-hexyl, 2-methylcyclopropyl, cyclopropylmethyl, cyclopentylmethyl, norbornyl, adamantyl, myrtanyl and the like. "Lower cycloalkyl" refers to cycloalkyl of 3 to 6 carbons.

$C_1$ to $C_{20}$ Hydrocarbon includes alkyl, cycloalkyl, alkenyl, alkynyl, aryl and combinations thereof. Examples include phenethyl, cyclohexylmethyl and naphthylethyl.

"Alkoxy" means alkoxy groups of from 1 to 8 carbon atoms of a straight, branched, cyclic configuration and combinations thereof. Examples of alkoxy groups include methoxy, ethoxy, propoxy, isopropoxy, cyclopropyloxy, cyclohexyloxy, and the like. "Lower alkoxy" means alkoxy having 1–4 carbon atoms.

"Halo" includes F, Cl, Br, and I.

"Fluoroalkyl" refers to an alkyl residue in which one or more hydrogen atoms are replaced with F, for example: trifluoromethyl, difluoromethyl, and pentafluoroethyl.

"Arylalkyl" denotes a residue comprising an alkyl attached to an aromatic or heteroaromatic ring. Examples include benzyl, phenethyl, 4-chlorobenzyl, and the like.

For the purpose of the present invention, the term "combinatorial library" means a collection of molecules based on logical design and involving the selective combination of building blocks by means of simultaneous chemical reactions. Each species of molecule in the library is referred to as a member of the library.

As will be obvious to the person of skill in the art, the linkers of the invention could be used in combinatorial synthesis to attach tags as well as to attach the moiety of putative chemical or pharmacological interest. Tags are chemical entities which possess several properties: they are detachable from the solid supports, preferably by means orthogonal to those employed for releasing the compound of pharmacological interest; they are stable under the synthetic conditions; and they are capable of being detected in very small quantities, e.g., $10^{-18}$ to $10^{-9}$ mole. Suitable tags and methods for their employment are described in U.S. Pat. No. 5,565,324, the entire disclosure of which is incorporated herein by reference.

The materials upon which combinatorial syntheses are performed are referred to as solid supports, beads, and resins. These terms are intended to include:

(a) beads, pellets, disks, fibers, gels, or particles such as cellulose beads, pore-glass beads, silica gels, polystyrene beads optionally cross-linked with divinylbenzene and optionally grafted with polyethylene glycol, polyacrylamide beads, latex beads, dimethylacrylamide beads optionally cross-linked with N,N'-bis-acryloyl ethylene diamine, glass particles coated with hydrophobic polymer, etc., i.e., material having a rigid or semi-rigid surface; and (b) soluble supports such as polyethylene glycol or low molecular weight, non-cross-linked polystyrene. The solid supports may, and usually do, have functional groups such as amino, hydroxy, carboxy, or halo groups; amino groups are the most common. Techniques for functionalizing the surface of solid phases are well known in the art. Attachment of lysine to the amino groups on a bead (to increase the number of available sites) and subsequent attachment of linkers as well as further steps in a typical combinatorial synthesis are described, for example, in PCT application WO95/30642, the disclosure of which is incorporated herein by reference. In the synthesis described in WO95/30642, the linker is a photolytically cleavable linker, but the general principles of the use of a linker are well illustrated. In carrying out the syntheses, one begins with at least $10^3$, desirably at least $10^4$, and generally not exceeding $10^{15}$ solid supports. Depending on the pre-determined number of choices of residues for the first step, one divides the supports accordingly into as many containers. The appropriate reagents and reaction conditions are applied to each container and the combination of identifiers which encode for each choice is added and attached. Depending on the chemistries involved, the tagging may be done prior to, concomitantly with, or after the reactions which comprise each choice. As a control, sample supports may be picked at any stage and a portion of their tags detached and decoded to verify that the correct tags are bound to the sample supports. As needed, one may wash the beads free of any excess reagents or by-products before proceeding. At the end of each step, the supports are usually combined, mixed, and again divided, this time into as many containers as pre determined for the number of choices for the second step in the synthesis. This procedure of dividing, reacting, tagging, and remixing is repeated until the combinatorial synthesis is completed.

SCHEME 1

Functionalized supports such as amino-functionalized or hydroxy-terminating PEG grafted polystyrene beads are divided into a pre-determined number of reaction vessels and are reacted with a cleavable linker/ligand element 3, which has been pre-formed, to generate 4. Unique tagging of the supports in each reaction vessel is achieved with combinations of identifiers encoded in a binary scheme. The identifiers are attached by adding a solution of the identifiers (in a 1.5% wt./wt. identifier:solid support ratio) to a batch of supports suspended in $CH_2Cl_2$ and shaking the mixture for 30 min. A dilute solution of rhodium trifluoroacetate dimer is added and the mixture is immediately shaken 4 hr and washed in $CH_2Cl_2$. The procedure is repeated and the mixture shaken for 14 hr and then washed in DMF/DCM.

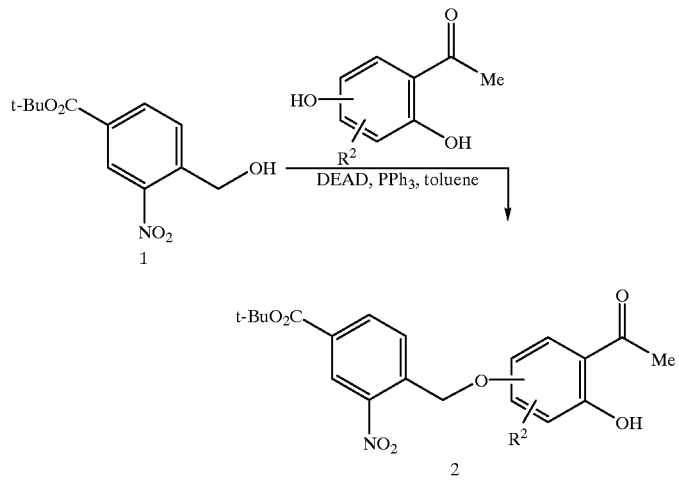

SCHEME 1
LINKER /1st LIGAND ELEMENT

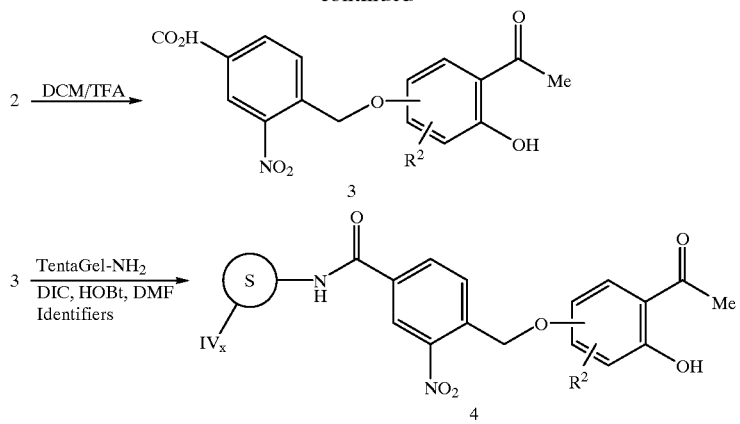

x is 1–30, depending on the binary code for the selected solid support

The compounds 4 are pooled, mixed, and divided into a pre-determined number of reaction vessels, each of which is treated with one reagent corresponding to further synthetic elements. Unique tagging of the supports in each reaction vessel is achieved with combinations of additional identifiers encoded in a binary scheme. Upon completion of the syntheses, the attached compounds are exposed to UV light (~360 nm) in polar solvents such as DMSO, $H_2O$, or a lower alkanol such as MeOH to cleave the compounds from the support/linker complex.

TENTAGEL™ resin may be modified with bis-Boc Lysine to increase the available reaction sites for ligand attachment Bis-Boc-lysine in DMF, HOBt, and DIC are shaken at r.t. and then dry TENTAGEL™ resin is added. The mixture is shaken at r.t. for 17 hr and then washed alternately with methanol and DCM and then with THF and dried under vacuum. To deprotect the resin, DCM is added, followed by a 30% TFA solution in DCM (100 mL). The vessel is shaken at room temperature for 15 min. before adding neat TFA. The vessel is shaken at room temperature for 2.5 hr at which time the resin is washed with DCM, then treated with a solution of 10% triethylamine in DCM, then washed with DCM and DMF.

In a 250 mL synthesis vessel was placed bis-Boc-(L)-lysine (7.71 g, 22.2 mmol) as a solution in DMF (150 mL). HOBt (2.4 g, 21.0 mmol) was added followed by DIC (3.25 mL, 21.0 mmol) and the solution shaken at r.t. for 15 min. before adding TENTAGEL™ resin (25.8 g, approximately 7.2 mmol amino sites). The mixture was shaken at r.t. for 17 hr and then washed alternately wit methanol and DCM (5× each) and then with THF (2×) and dried under vacuum.

Into each of seven 250 mL synthesis vessel was placed modified TENTAGEL™ resin (8.0 g, approx. 4.5 mmol of N-Boc amine sites). DCM (75 mL) was added followed by a 30% TFA solution in DCM (100 mL). The vessel was shaken at room temperature for 15 min before adding neat TFA (15 mL). The vessel was shaken at room temperature for 2.5 hr at which time the resin was washed with DCM (2×). The resin was then treated with a solution of 10% triethylamine in DCM (2×150 mL) shaking for 20 min. each time. The resin was then washed with DCM(4×) and DMF (1×).

In an appropriately sized synthesis vessel is placed HOBt (3 equiv.) and the carboxylic acid(3 equiv.) in a solvent such as DMF. DIC (3 equiv.) is added and the vessel agitated for 15 min. before adding the amino resin (1 equiv. of amino sites). The resin is agitated for 5 hrs., then washed with alternating DCM and MeOH (5× each) and then with THF (2×) to yield resin with the linker/ligand attached.

Alternatively, in an appropriately sized synthesis vessel is placed the amino resin (1 equiv. of amino sites). A solvent such as DCM is added, followed by an organic base such as triethylamine, pyridine, Hunig's base (di-isopropylethylamine), or 2,6-lutidine (10 equiv.). The resin is agitated for 15 min. before adding an acid halide (5 equiv.) as a dilute solution in a solvent such as DCM. The resin is agitated for 4 hrs. and then washed with DCM and MeOH (5× each) to yield resin with the linker/ligand attached.

The invention relates to substrates for solid phase synthesis comprising solid phase-linker combinations of the formula:

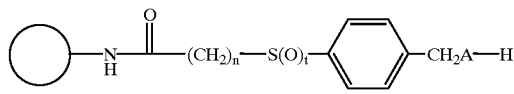

In these solid phase-linker combinations, t=1 at the beginning of solid phase synthesis and t is reduced to t=0 when it is desired that the linker can be cleaved. The relative stability of the sulfoxide (t=1) allows the use in solid phase synthesis of acids and bases that would cleave an alkylthiobenzyl linkage. We refer to these linkers as "universal linkers" because of their stability to both basic and acidic conditions. When the elaboration of the attached moiety is complete, the sulfoxide may be reduced under very mild conditions to a thioether. The thioether activates the benzyl alcohol (or amine, depending on the nature of A) toward acid cleavage. The linker can then be acid cleaved without harm to the compounds being synthesized and without damage to the support.

The solid phase-linker combinations are prepared by the following route:

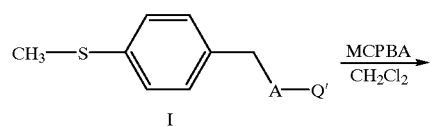

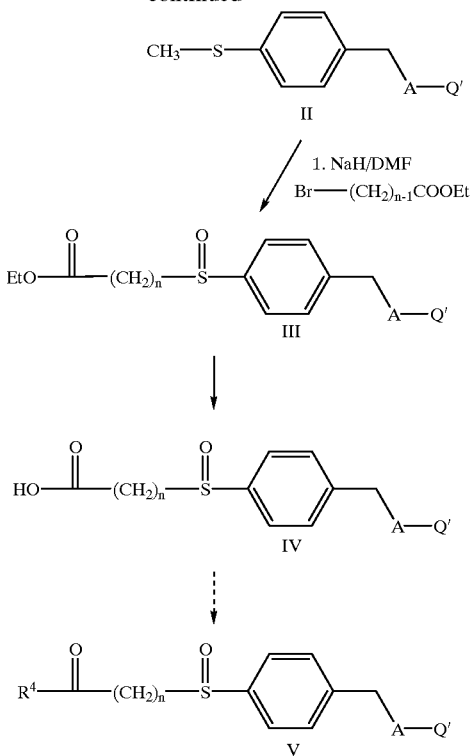

Commercially available 4-(methylthio)benzyl alcohol or benzylamine is protected with any of the well-known protecting groups for alcohols or amines. [See Greene and Wuts *Protective Groups in Organic Synthesis* Second Edition John Wiley & Sons, New York 1991, pages 1–118 and 309–370]. Preferred protecting groups are t-butyldiphenylsilyl for the benzyl alcohol and t-BOC for the amine. Methods for protecting and deprotecting with these groups are found in Greene and Wuts on pages 83 and 327 respectively.

The suitably protected 4-(methylthio)benzyl alcohol or benzylamine I is oxidized with a slight excess of meta-chloroperbenzoicacid (MCPBA) in an inert solvent such as dichloromethane. Other oxidants for converting thioethers to sulfoxides are known and could be used, but MCPBA is convenient. The resulting sulfoxide II is deprotonated with a strong base, such as sodium hydride in DMF, and alkylated on carbon with an ω-bromoalkanoate ester of one fewer carbons than the desired chain length. Methyl and ethyl esters are preferred. An alternative route to the same ester-sulfoxide III is via the alkylation of the protected 4-mercaptobenzyl alcohol or amine with an ω-bromoalkanoate ester of the same number of carbons as the desired chain length followed by oxidation with MCPBA. Lower alkyl ω-haloalkylcarboxylates are readily prepared by procedures known in the art, and most of those in the C-4 to C-10 range are commercially available. In preferred embodiments, the lower alkyl ω-haloalkylcarboxylate is ethyl 4-bromobutyrate.

The ester III is saponified with an aqueous base, preferably an alkali metal hydroxide, such as lithium hydroxide, and the pH may be controlled, e.g. by means of an autotitrator.

The acid IV may be directly condensed with the amino functionality on the solid support, or an activated derivative V may be preformed. Condensing agents for reacting amines (the resin) with carboxylic acids (the linker) are well known, particularly in the art of solid phase synthesis of peptides. Such agents include carbodiimides of various sorts, mixed anhydrides, EEDQ, HATU, and the like. It is also possible to pre-react the carboxylic acid of the linker with an appropriate leaving group to form an activated ester. Activated esters denote esters which are capable of undergoing a substitution reaction with primary or secondary amines to form an amide. The term includes esters "activated" by neighboring electron withdrawing substituents. Examples include esters of phenols, particularly electronegatively substituted phenol esters such as pentafluorophenol esters; O-esters of isourea, such as arise from interaction with carbodiimides; O-esters of N-hydroxyimides and N-hydroxy heterocycles; specific examples include S-t-butyl esters, S-phenyl esters, S-2-pyridyl esters, N-hydroxypiperidine esters, N-hydroxysuccinimide esters, N-hydroxyphthalimide esters and N-hydroxybenzotriazole esters. Solvents that are inert to the conditions of the condensation are "suitable solvents". These include, for example, THF, DMF, DCM and the like.

For combinatorial synthesis, the solid phase-linker combination may be reacted with a carboxylic acid, an alkyl halide or any other substituent known to react with an alcohol or amine. The choice of reagent is immaterial to the present invention and is determined by the nature of the combinatorial library sought to be synthesized. The number and nature of further reactions of support-linked synthon will be similarly dictated by the needs of the library. When the combinatorial synthesis is complete, the sulfoxide in the linker can be reduced with a trivalent phosphorus reagent and the linker cleaved from the resin by treatment with acid, preferably trifluoroacetic acid in dichloromethane, or HCl in diethyl ether or dioxane.

We claim:

1. A chemical intermediate of the formula

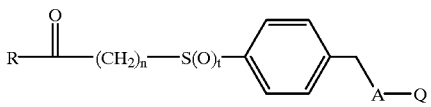

wherein n is 3–20;

t is selected from the group consisting of 0 and 1;

A is selected from the group consisting of —O— and —NH—;

Q is selected from the group consisting of hydrogen, a protecting group for an amine and a protecting group for an alcohol; and R is chosen from OH, the residue of a solid support having a plurality of amino functionalities, and a residue of an activated ester.

2. A chemical intermediate according to claim 1 wherein R is OH.

3. A chemical intermediate according to claim 1 wherein R is selected from the group consisting of

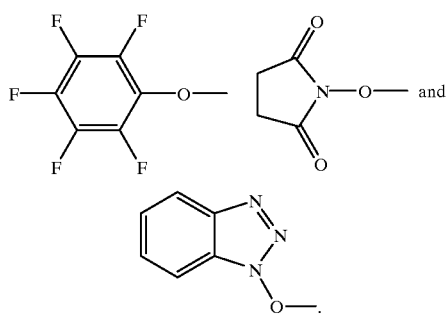

4. A chemical intermediate according to claim 1 wherein R is the residue of a solid phase substrate chosen from aminomethylated poly(styrene-co-divinylbenzene) and divinylbenzene-cross-linked, polyethyleneglycol-grafted polystyrene functionalized with amino groups.

5. A chemical intermediate according to claim 1 wherein A is —NH— and Q is t-butoxycarbonyl, or benzyloxycarbonyl.

6. A chemical intermediate according to claim 1 wherein A is —O— and Q is t-butyl, alkylcarbonyl, arylcarbonyl, benzyl, tetrahydropyranyl or trialkylsilyl.

7. A chemical intermediate according to claim 1 wherein n is 3–5.

* * * * *